United States Patent [19]

Erickson et al.

[11] Patent Number: 5,359,098

[45] Date of Patent: Oct. 25, 1994

[54] INTERMEDIATES FOR MAKING SIGMA BINDING SITE AGENTS

[75] Inventors: Ronald H. Erickson; Kenneth J. Natalie, Jr., both of Baltimore; Michael J. Pontecorvo, So. Belcamp; Waclaw J. Rzeszotarski, Millersville, all of Md.

[73] Assignee: Guilford Pharmaceuticals Inc., Baltimore, Md.

[21] Appl. No.: 151,825

[22] Filed: Nov. 15, 1993

Related U.S. Application Data

[60] Division of Ser. No. 700,296, May 17, 1991, Pat. No. 5,278,174, which is a continuation-in-part of Ser. No. 533,127, Jun. 4, 1990, abandoned.

[51] Int. Cl.$^5$ ............................................. C07D 311/76
[52] U.S. Cl. ........................................ 549/400; 549/401; 549/403
[58] Field of Search ............... 549/401, 403, 408, 400, 549/60; 546/167, 269

[56] References Cited

U.S. PATENT DOCUMENTS

| | | | |
|---|---|---|---|
| 3,046,275 | 7/1962 | Kohlstaedt et al. | 544/151 |
| 3,705,167 | 12/1972 | Malen et al. | 546/202 |
| 3,810,896 | 5/1974 | Witte et al. | 260/268 |
| 3,835,175 | 9/1974 | Carpino et al. | 558/282 |
| 3,864,362 | 2/1975 | Feuer | 549/401 |
| 3,906,031 | 9/1975 | Carpino et al. | 560/32 |
| 3,907,830 | 9/1975 | Feuer | 549/401 |
| 4,163,746 | 8/1979 | Feuer | 549/401 |
| 4,376,123 | 4/1983 | Hausberg et al. | 546/206 |
| 4,394,519 | 7/1983 | Carpino et al. | 560/32 |
| 4,678,787 | 7/1987 | Jaen et al | 514/253 |
| 4,780,478 | 10/1988 | Hausberg et al. | 514/456 |
| 4,797,498 | 1/1989 | Albrecht et al. | 549/403 |
| 4,900,727 | 2/1990 | Kattige et al. | 514/212 |

FOREIGN PATENT DOCUMENTS

| | | |
|---|---|---|
| 928298 | 6/1973 | Canada . |
| 1154444 | 9/1983 | Canada . |
| 90055 | 2/1961 | Denmark . |
| 190015 | 1/1986 | European Pat. Off. . |
| 1018874 | 11/1957 | Fed. Rep. of Germany . |
| 1054091 | 4/1959 | Fed. Rep. of Germany . |
| 1222072 | 8/1966 | Fed. Rep. of Germany . |
| 1223849 | 9/1966 | Fed. Rep. of Germany . |
| 920380 | 3/1963 | United Kingdom . |

OTHER PUBLICATIONS

Clark et al. "Principles of Psychopharmacology" Academic Press, pp. 166–167 (1970).

Hackh's "Chemical Dictionary" McGraw Hill, 1983, p. 27.

Wu, E. S. C. et al., *J. Med. Chem.* (1989), vol. 32, pp. 183–192.

Jesthi, P. K. et al., *J. Indian Chem. Society* (1965), vol. 42, pp. 105–108.

Chouinard, G. and Annable, L. *Psychopharmacol.* (1984), vol. 84, pp. 282–284.

Klosa, V. J. *J. Prak. Chem.* (1963), vol. 22, p. 259.

Bayer, E. and Krämer, B., *Chem. Ber.* (1964), vol. 97, pp. 1057–1068.

Szegi, J. et al. *Congr. Hung. Pharmacol. Soc.* [Proc.] (1971), p. 221.

Hetenyi, E. L. et al., *Acta Pharm. Hung.* (1974), vol. 44, p. 1.

(List continued on next page.)

*Primary Examiner*—Celia Chang
*Attorney, Agent, or Firm*—Nath, Amberly & Associates

[57] ABSTRACT

Sigma binding site agents having the formula

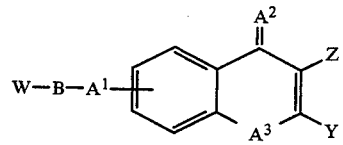

wherein $A^1$, $A^2$, $A^3$, B, y and 2 are defined in the specification, W is halogen, which are novel intermediates useful in preparing the presently binding site agents.

17 Claims, No Drawings

OTHER PUBLICATIONS

Da Re et al., *J. Med. Chem.* (1972), vol. 15, No. 8, pp. 868–869.
Briggs, M. T. et al., *J. Chem. Res. Synop.* (1982), p. 242.
*Chem. Abstracts,* 99:139772 (1983).
*Chem. Abstracts,* 94:65430 (1981).
*Chem. Abstracts,* 63:9918c–9921d (1965).
*Chem. Abstracts,* 104:50791 (1986).
Martin, W. R. et al., *J. Pharm. Exp. Ther.,* vol. 197, No. 3 (1976), pp. 517–532.
*Chem. Abstracts,* 79:126312c (1973).
*Chem. Abstracts,* 60:5441d (1963).
Hetenyi, E. *Kiserl. Orvostud.* (1968) 20, 534.
Ji et al., *Acta Pharm. Sin.* (1989), vol. 24:12, pp. 906–912.
Ferrani, G. et al., *J. Med. Chem.* (1966), vol. 9, pp. 979–980.
Moersch, G. W. et al., *J. Med. Chem.* (1967), vol. 10, pp. 154–158.
Jaen, J. C. et al., *J. Med. Chem.* (1991), vol. 34, pp. 248–256.

INTERMEDIATES FOR MAKING SIGMA BINDING SITE AGENTS

RELATED APPLICATION

This application is a division of U.S. patent application Ser. No. 07/700,296, filed May 17, 1991, now U.S. Pat. No. 5,278,174, which is a continuation-in-part of U.S. patent application Ser. No. 07/533,127, filed Jun. 4, 1990 and now abandoned.

BACKGROUND OF THE INVENTION

1. Field of the Invention

This invention relates to novel compounds that are sigma binding site agents.

2. Background Information

Use of drugs with well-demonstrated effectiveness in treatment of psychiatric disorders has become widespread over the last thirty years. Presently about twenty percent of the prescriptions written in the United States are for medications intended to change mood, thinking, or behavior. Neuroleptic agents such as chlorpromazine and haloperidol are the primary medications used to treat schizophrenia and other psychoses. Most of the numerous clinically effective antipsychotic drugs currently available are dopamine ($D_2$) receptor antagonists and produce essentially the same spectrum of adverse effects. Examples of adverse effects include extrapyramidal side effects such as various dystonias which may resemble Parkinson's disease. Tardive Dyskinesia, characterized by involuntary movements consisting of sucking and smacking of the lips, lateral jaw movements, and fly-catching dartings of the tongue, is a serious and potentially irreversible adverse effect which occurs in up to twenty percent of patients treated with currently available antipsychotic agents.

The recently identified central nervous system sigma binding sites are potential targets for development of antipsychotic drugs that lack the adverse effects associated with available $D_2$ antagonists. Sigma binding sites were initially postulated by Martin et al., *J. Pharmacol. Exp. Ther.*, 197: 517-532, 1976, to explain the psychotomimetic effects of(+)-benzomorphans such as N-allynormetazocine (SK&F 10047). It was subsequently demonstrated that sigma sites could be selectively labeled by the ligands [$^3$H]ditolylguanidine (DTG) and [$^3$H] (+)-3-(hydroxyphenyl)-N-(1-propyl)piperidine [(+)-3-PPP]. Both psychotomimetic agents, such as the (+)benzomorphans and PCP, and certain antipsychotic drugs, including haloperidol, displace [$^3$H]DTG and [$^3$H](+)-3-PPP from sigma sites. Because haloperidol reverses the stimulant and psychotomimetic effects of SK&F 10047 and PCP, it has been argued that haloperidol may be a sigma "antagonist" and that the sigma "antagonist" activity of this and related agents may contribute to their antipsychotic effects. Thus, a selective sigma "antagonist" that, unlike haloperidol, is relatively inactive at dopamine receptors could evidence antipsychotic activity without producing extrapyramidal side effects or tardive dyskinesias associated with currently available dopamine antagonist neuroleptics.

Rimcazole is the first sigma-selective antipsychotic for which results of a substantial number of clinical trials have been reported. Although rimcazole has shown some effectiveness in treating schizophrenia, it is only moderately potent at sigma sites and has been shown to induce seizures. Chouniard, G. and L. Annable, *Psychopharmacol.* 84: 282-284 (1984); Guy, W. et al., *Drug Dev. Res.* 3: 245-252 (1983). Remoxipride, another sigma site binding agent which has been tested in humans, also has significant $D_2$ blocking potency. Thus, there remains a need for sigma-selective agents which effectively treat psychoses without producing adverse effects.

It has now been found that certain derivatives of chromone (4H-1-benzopyran-4-one) compounds (Formula I, below) are potent and selective for sigma binding sites and, like haloperidol, antagonize the stimulant/psychotomimetic effects of the dopamine agonist, amphetamine, and presumed sigma agonists such as PCP. For this reason, the novel chromones, like haloperidol, will be referred to as sigma antagonists. Note that the designation of these agents as sigma antagonists refers to the in vivo pharmacological profile of the compounds, not to the mechanism of action at sigma receptors/binding sites. Also, "receptor" as used herein refers to true, membrane-bound receptors and to other binding sites.

Jesthi, P. K. et al. describe β-diethylaminoacetoxy, β-aminoethoxy, and β-diethylaminoethoxy flavone derivatives found to possess antispasmodic and antihistaminic properties. *J. Indian Chem. Soc.* 42: 105-108 (1965).

German Patent No. 1,054,091 (1959) discloses a series of N-substituted-2-phenyl-7-aminoalkoxy chromone compounds reported to have vasodilator activity.

U.S. Pat. No. 3,810,896 (1974) discloses various 4-[ω-(flavone-7-yloxy)]-alkyl piperazine compounds reported to have antiinflammatory and antiedematous action.

U.S. Pat. No. 4,678,787 (1987) discloses 4H-1-benzopyran-4-ones and their sulfur analogues for treatment of psychosis including schizophrenia.

SUMMARY OF THE INVENTION

The present invention resides in the discovery that certain derivatives of chromone compounds of Formula I (below) are potent and selective sigma receptor binding site agents which, like haloperidol, antagonize the stimulant/psychotomimetic effects of dopamine agonists, such as amphetamine, and presumed sigma agents such as phencyclidine. These compounds are useful as antipsychotic drugs.

Illustrative compounds of the invention include:
6-[6-(4-hydroxypiperidinyl)hexoxy]-3-methyl-2-phenyl-4H-1-benzopyran-4-one,
6-[6-(4-hydroxypiperidinyl)hexoxy]-2-phenyl-4H-1-benzopyran-4-one,
6-[8-(dimethylamino)octoxyl]-2-phenyl-4H-1-benzopyran-4-one,
6-[5-(dimethylamino)pentoxy]-2-phenyl-4H-1-benzopyran-4-one,
6-[6-(dimethylamino)hexoxy]-2-phenyl-4H-1-benzopyran-4-one,
6-[6-(2-hydroxyethylmethylamino)hexoxy]-2-phenyl-4H-1-benzopyran-4-one,
6-[7-(dimethylamino)heptoxy]-2-phenyl-4H-1-benzopyran-4-one,
6-[9-(dimethylamino)nonoxy]-2-phenyl-4H-1-benzopyran-4-one,
6-[9-(4-methylpiperazinyl)nonoxy]-2-phenyl-4H-1-benzopyran-4-one,
6-[10-(dimethylamino)decoxy]-2-phenyl-4H-1-benzopyran-4-one, 6-[5-(4-hydroxypiperidinyl)pentoxy]-2-(3-methoxyphenyl)-4H-1-benzopyran-4-one,
6-[5-(4-hydroxypiperidinyl)pentoxy]-2-(4-methoxyphenyl)-4H-1-benzopyran-4-one,
2-(3,4-dimethoxyphenyl)-6-[5-(4-hydroxypiperidinyl)pentoxy]-4H-1-benzopyran-4-one,
2-cyclohexyl-6-[5-(4-hydroxypiperidinyl)pentoxy]-4H-1-benzopyran-4-one,
6-[5-(dipropylamino)pentoxy]-2-(3-methoxyphenyl)-4H-1-benzopyran-4-one,
6-[5-(dipropylamino)pentoxy]-2-(4-methoxyphenyl)-4H-1-benzopyran-4-one,
2-(3,4-dimethoxyphenyl)-6-[5-(dipropylamino)pentoxy]-4H-1-benzopyran-4-one,
6-[5-(4-hydroxypiperidinyl)pentoxy]-2-phenyl-4H-1-benzopyran-4-one,
6-[7-(4-hydroxypiperidinyl)heptoxy]-2-phenyl-4-H-1-benzopyran-4-one,
7-[4-(dimethylamino)butoxy]-2-phenyl-4H-1-benzopyran-4-one,
5-[6-(dimethylamino)hexoxy]-2-phenyl-4H-1-benzopyran-4-one,
6-[5-(4-hydroxypiperidinyl)pentoxy]-2-phenyl-4H-1-benzopyran-4-one,
6-[4-(4-hydroxypiperidinyl)butoxy]-2-phenyl-4H-1-benzopyran-4-one,
6-[5-(4-hydroxypiperidinyl)pentoxy]-2-isobutyl-4H-1-benzopyran-4-one,
6-[8-(4-hydroxypiperdinyl)octoxy]-2-phenyl-4H-1-benzopyran-4-one,
2-(3-fluorophenyl)-6-[6-(4-hydroxypiperdinyl)hexoxy]-4H-1-benzopyran-4-one,
2-cyclohexyl-6-[6-(4-hydroxypiperidinyl)hexoxy]-4H-1-benzopyran-4-one,
6-[6-(4-hydroxypiperdinyl)hexoxy]-2-(3-methoxyphenyl)-4H-1-benzopyran-4-one,
2-phenyl-6-(6-piperidinylhexoxy)-4H-1-benzopyran-4-one,
6-(6-morpholinylhexoxy)-2-phenyl-4H-1-benzopyran-4-one,
2-cyclopentyl-6-[6-(4-hydroxypiperidinyl)hexoxy]-4H-1-benzopyran-4-one,
2-(4-chlorophenyl)-6-[6-(4-hydroxypiperidinyl)hexoxy]-4H-1-benzopyran-4-one,
2-(3-chlorophenyl)-6-[6-(4-hydroxypiperidinyl)hexoxy]-4H-1-benzopyran-4-one,
6-[6-(4-hydroxypiperidinyl)hexoxy]-(4-methoxyphenyl)-4H-1-benzopyran-4-one,
2-cyclohexyl-6-(6-piperidinylhexoxy)-4H-1-benzopyran-4-one,
2-cyclohexyl-6-(6-morpholinylhexoxy)-4H-1-benzopyran-4-one,
7-[5-(4-hydroxypiperidinyl)pentoxy]-2-phenyl-4H-1-benzopyran-4-one,
7-[6-(4-hydroxypiperidinyl)hexoxy]-2-phenyl-4H-1-benzopyran-4-one,
6-[6-(4-(4-chlorophenyl)-1,2,3,6-tetrahydropyridyl)hexoxy]-2-phenyl-4H-1-benzopyran-4-one,
2-cyclohexyl-6-[6-(4-hydroxypiperidinyl)hexoxy]-3-methyl-4H-1-benzopyran-4-one,
6-[6-(4-(4-chlorophenyl )-4-hydroxypiperidinyl)hexoxy]-2-cyclopentyl-4H-1-benzopyran-4-one,
2-cyclopentyl-6-(6-piperidinyl)hexoxy-4H-1-benzopyran-4-one,
2-(4-fluorophenyl)-6-[6-(4-hydroxypiperidinyl) hexoxy]-4H-1-benzopyran-4-one,
2-cyclobutyl-6-[6-(4-hydroxypiperidinyl)hexoxy]-4H-1-benzopyran-4-one,
2-cyclobutyl-6-(6-piperidinylhexoxy)-4H-1-benzopyran-4-one,
6-[6 -(4-(4-chlorophenyl)-4-hydroxypiperidinyl)hexoxy]-2-cyclobutyl-4H-1 -benzopyran-4-one,
2-(3-chlorophenyl)-6-[6-(4-(4-chlorophenyl)-4-hydroxypiperidinyl)hexoxy]-4H-1-benzopyran-4-one,
2-(3-chlorophenyl)-6-(6-piperidinyl) hexoxy-4H-1-benzopyran-4-one,
2-(3-chlorophenyl)-6-[6-(4-hydroxypiperidinyl) hexoxy]-4H-1-benzopyran-4-one,
6-[6-(4-hydroxypiperidinyl)hexoxy]-2-(2-thienyl)-4H-1-benzopyran-4-pyran-4-one,
6-(6-piperidinyl)-2-(2-thienyl)-4H-1-benzopyran-4-one,
6-[6-(4-(4-chlorophenyl)-4-hydroxypiperidinyl) hexoxy]-2-(2-thienyl)-4H-1-benzopyran-4-one,
6-[6-(4-methylpiperidinyl)hexoxy]-2-phenyl-4H-1-benzopyran-4-one,
(±)-6-[6-(3-hydroxypiperidinyl) hexoxy]-2-phenyl-4H-1-benzopyran-4-one,
6-[6-(4-hydroxypiperidinyl)hexoxy]-3-methoxy-2-phenyl-4H-1-benzopyran-4-one,
5-[4-(4-Hydroxypiperidinyl)butoxy]-2-phenyl-4H-1-benzopyran-4-one,
5-[5-(4-hydroxypiperidinyl)pentoxy]-2-phenyl-4H-1-benzopyran-4-one,
5-[3-(4-hydroxypiperidinyl)propoxy]-2-phenyl-4H-1-benzopyran-4-one,
6-[6-(N,N-Benzylmethylamino)hexoxy]-2-phenyl-4H-1-benzopyran-4-one,
6-(Pyrrolidylhexoxy)-2-phenyl-4H-1-benzopyran-4-one,
6-(6-Hexamethyleneiminohexoxy)-2-phenyl-4H-1-benzopyran-4-one,
5-[6-(4-hydroxypiperidinyl)hexoxy]-2-phenyl-4H-1-4-one,
6-[6-(4-(2-Hydroxyethyl)piperazinyl)hexoxy]-2-phenyl-4H-1-benzopyran-4-one,
6-[5-(Dimethylamino)pentoxy]-2-phenyl-4H-1-benzopyran-4-one,
6-[6-(Diethylamino)hexoxy]-2-phenyl-4H-1-benzopyran-4-one,
6-[6-(4-(4-Chlorophenyl)piperazinyl)hexoxy]-2-phenyl-4H-1-benzopyran-4-one,
7-[8-(4-Hydroxypiperidinyl)octoxy]-2-phenyl-4H-1-benzopyran-4-one,
7-[4-(4-hydroxypiperidinyl)butoxy]-2-phenyl-4H-1-benzopyran-4-one,
7-[7-(4-hydroxypiperidinyl)heptoxy]-2-phenyl-4H-1-benzopyran-4-one,
6-(6-piperidinylhexoxy)-2-(3-pyridyl)-4H-1-benzopyran-4-one,
6-(6-piperidinylhexoxy)-2-(4-pyridyl)-4H-1-benzopyran-4-one,
6-[6-(4-Hydroxypiperidinyl)hexoxy]-2-(4-pyridyl)-4H-1-benzopyran-4-one,
6-[6-(4-Hydroxypiperidinyl)hexoxy]-2-(3-pyridyl)-4H-1-benzopyran-4-one,
6-[4-dimethylamino)butoxy]-2-phenyl-4H-1-benzopyran-4-one,
6-[5-(4-hydroxypiperidinyl)pentoxyl]-2-(3,4-dimethoxyphenyl)-4H-1-benzopyran-4-one,
6-[5-(4-hydroxypiperidinyl)pentoxyl]-2-cyclohexyl-4H-1-benzopyran-4-one,
6-[5-(dipropylamino)pentoxyl]-2-(4-methoxyphenyl)-4H-1-benzopyran-4-one,
6-[5-(dipropylamino)pentoxyl]-2-(3,4-dimethoxyphenyl)-4H-1-benzopyran-4-one, 6-[6-(4-hydroxypiperidinyl)hexoxy]-2-cyclohexyl-4H-1-benzopyran-4-one,
2-(4-chlorophenyl)-6-[6-(4-hydroxypiperidinyl)hexoxy-4H-1-benzopyran-4-one,
6-[6-(4-(4-chloropentyl)-1,2,3,6-tetrahydropyridyl)hexoxy]-2-phenyl-4H-1-benzopyran-4-one,
6-[6-(4-(4-chlorophenyl)-4-hydroxypiperidinyl)hexoxy]-2-cyclophenyl-4H-1-benzopyran-4-one,
2-(3-chlorophenyl)-6-[6-(4-(4-chlorophenyl)-4-hydroxypiperidinyl)hexoxy]-4H-1-benzopyran-4-one,
and their pharmaceutically acceptable salts and hydrates.

Preferred compounds of the invention include:
5-[6-(dimethylamino)hexoxy]-2-phenyl-4H-1-benzopyran-4-one,
7-[5-(4-hydroxypiperidinyl)pentoxy]-2-phenyl-4H-1-benzopyran-4-one,
7-[6-(4-hydroxypiperidinyl)hexoxy]-2-phenyl-4H-1-benzopyran-4-one,
5-[6-(dimethylamino)hexoxy]-2-phenyl-4H-1-benzopyran-4-one,
7-[5-(4-hydroxypiperidinyl)pentoxy]-2-phenyl-4H-1-benzopyran-4-one,
7-[6-(4-hydroxypiperidinyl)hexoxy]-2-phenyl-4H-1-benzopyran-4-one,
5-[4-(4-Hydroxypiperidyl)butoxy]-2-phenyl-4H-1-benzopyran-4-one,
5-[5-(4-hydroxypiperidinyl)pentoxy]-2-phenyl-4H-1-benzopyran-4-one,
5-[3-(4-hydroxypiperidinyl)propoxy]-2-phenyl-4H-1-benzopyran-4-one,
5-[6-(4-hydroxypiperidinyl)hexoxy]-2-phenyl-4H-1-benzopyran-4-one,
7-[8-(4-Hydroxypiperidinyl)octoxy]-2-phenyl-4H-1-benzopyran-4-one,
7-[4-(4-hydroxypiperidinyl)butoxy]-2-phenyl-4H-1-benzopyran-4-one,
7-[7-(4-hydroxypiperidinyl)heptoxy]-2-phenyl-4H-1-benzopyran-4-one; or
one of their pharmaceutically acceptable salts or hydrates.

Preferred compounds of the invention also include:
2-cyclohexyl-6-(6-piperidinylhexoxy)-4H-1-benzopyran-4-one,
6-[-6-(4-hydroxypiperidinyl)-hexoxy]-3-methyl-2-phenyl-4H-1-benzopyran-4-one,
2-cyclohexyl-6-[6-(4-hydroxypiperidinyl)hexoxy)-3-methyl-4H-1-benzopyran-4-one,
2-cyclopentyl-6-(6-piperidinyl)hexoxy-4H-1-benzopyran-4-one,
or one of their pharmaceutically acceptable salts or hydrates.

DETAILED DESCRIPTION OF THE INVENTION

The presently invented compounds that bind at sigma sites have the following Formula I:

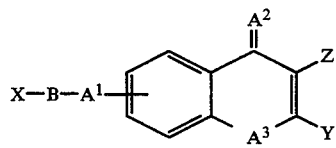

in which:
X is —NR¹R²,

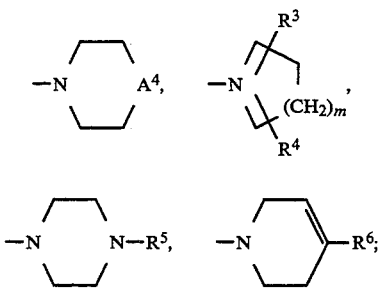

$R^1$ and $R^2$ are selected from the group consisting of —H, —$C_{1-6}$alkyl, a hydroxy-substituted $C_{1-6}$alkyl, and benzyl, provided $R^1$ and $R^2$ are not H;

$R^3$ and $R^4$ are selected from the group consisting of —H, —OH, $C_{1-4}$ alkyl, hydroxy-substituted $C_{1-4}$ alkyl, benzyl, phenyl optionally substituted with —OH, —Cl, —F, —O$C_{1-4}$alkyl, —$C_{1-4}$ alkyl, —$CF_3$, and any accessible combination thereof;

$R^5$ is selected from the group consisting of —H, —$C_{1-6}$ alkyl, hydroxy-substituted $C_{1-6}$ alkyl, phenyl optionally substituted with —OH, —Cl, —F, —O$C_{1-4}$alkyl, —$CF_3$, and any accessible combination thereof;

$R^6$ is selected from the group consisting of phenyl optionally substituted with —OH, —Cl, —F, —O$C_{1-4}$ alkyl, —$C_{1-4}$ alkyl, —$CF_3$, and any accessible combination thereof;

m is 1, 2, or 3;

$A^1$, $A^2$, $A^3$, and $A^4$ independently are O or S;

Y is selected from the group consisting of cyclo$C_{3-7}$ alkyl, $C_{1-6}$alkyl, thienyl, pyridyl, furanyl, quinolyl, phenyl optionally substituted with —OH, —Cl, —F, —O$C_{1-4}$ alkyl, $C_{1-4}$ alkyl, —$CF_3$, and any accessible combination thereof;

Z is —H, $C_{1-4}$ alkyl, or —O$R^7$;

$R^7$ is —H or $C_{1-4}$ alkyl; and

B is $C_{4-10}$ alkyl;

or pharmaceutically acceptable salts or hydrates thereof; provided that when B is $(CH_2)_4$, X is not $N(CH_3)_2$, $N(CH_2CH_3)_2$, piperidinyl, morpholinyl, pyrrolidinyl, or substituted piperazinyl.

As used in the specification and claims "accessible combination thereof" means any combination of substituents that is available by chemical synthesis and is stable and $C_{I-I'}$ alkyl means a straight or branched, saturated or unsaturated hydrocarbon having I to I' carbon atoms where I and I' are integers.

Preferred compounds have the following Formula (II)

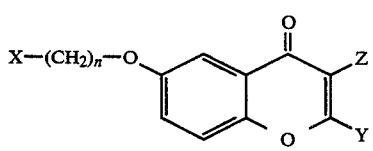

in which n is 4 to 10 and X, Y, and Z are as defined in Formula I. Also preferred are Formula I or Formula II compounds wherein B is $C_{5-10}$ alkyl, especially $C_{5-8}$ alkyl and $C_6$ alkyl.

Other preferred compounds are Formula II compounds wherein Z is —$CH_3$ or other $C_{1-4}$ alkyl, or —O$R^7$ and Y is phenyl. Especially preferred are such compounds wherein X is 4-hydroxypiperidinyl or piperidinyl, particularly those wherein Z is $CH_3$.

In another preferred embodiment when X is $-NR^1R^2$,

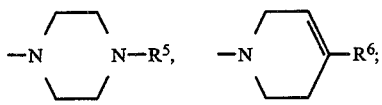

as defined herein, and Z is hydrogen then Y is not a $C_{1-6}$ alkyl.

Formula I compounds are prepared from corresponding substituted hydroxychromone compounds by processes such as shown in Scheme I, below. The starting hydroxychromone compounds are known and described in published references and can be purchased or readily prepared. In Scheme I, $Z^1$ and $Y^1$ are Z and Y in Formula I or substituents readily convertible to Z and Y.

Scheme I illustrates reaction of a substituted hydroxy chromone (A) with 1-bromo-5-chloropentane to yield a substituted chloropentoxy chromone (B). In this reaction 1-bromo-5-chloropentane is replaced by selected dihalo $C_{4-10}$ alkyls to yield Formula I compounds wherein B is other than $(CH_2)_5$.

Formula (B) compounds are then reacted with, for example, sodium iodide to yield compounds of Formula (C). Formula (D) compounds are prepared by reacting Formula (C) compounds with 4-hydroxypiperidine or are prepared by reacting Formula (B) compounds in the presence of sodium iodide with an amine selected to yield the desired X substituent. Scheme 1 shows reaction with 4-hydroxypiperidine to yield (4-hydroxypiperidinyl)pentoxy compounds.

Formula I compounds wherein $A^2$ or $A^3$ are sulfur are prepared by replacing the Formula (A) compounds with their sulfur analogues. These sulfur analogues also are known and described in published references and can be purchased or readily prepared. Formula I com-

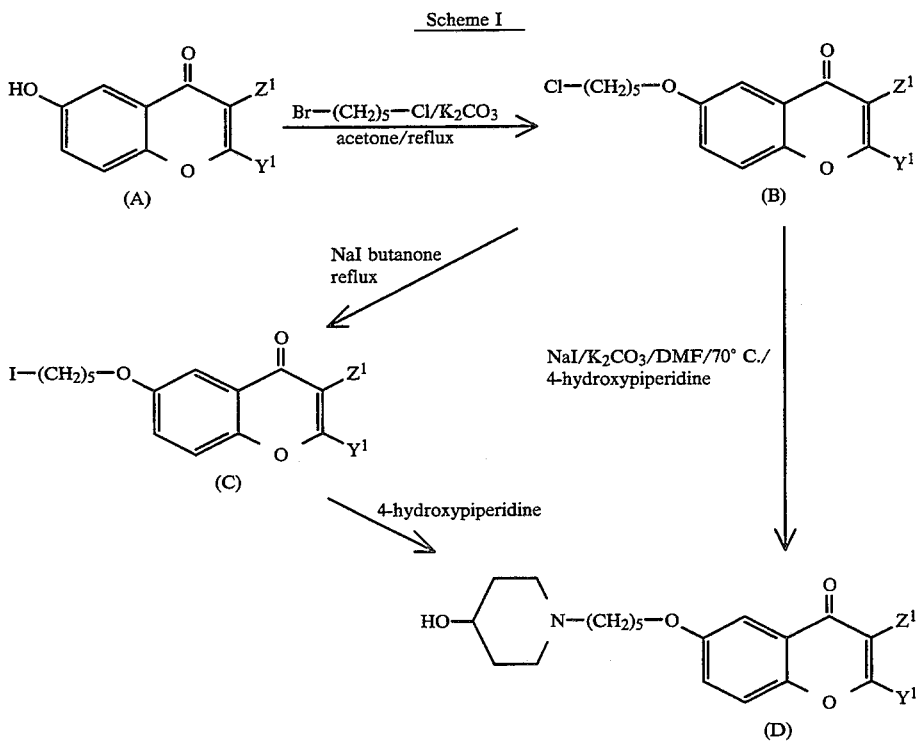

pounds where $A^1$ is sulfur are prepared by substituting Formula (A) compounds with their thiol analogues.

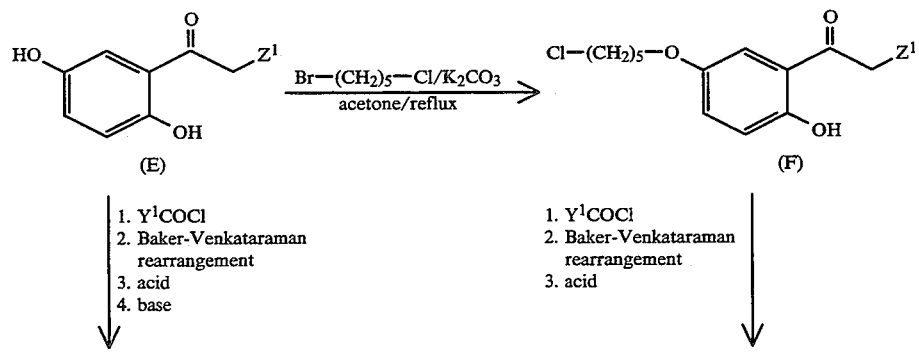

Scheme II

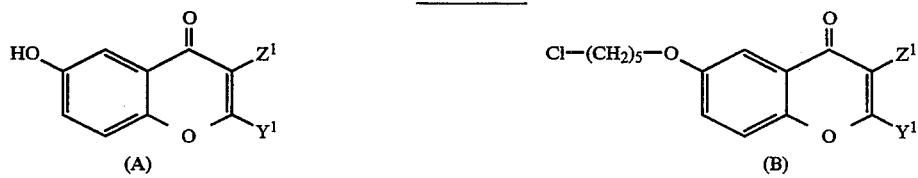

Scheme III

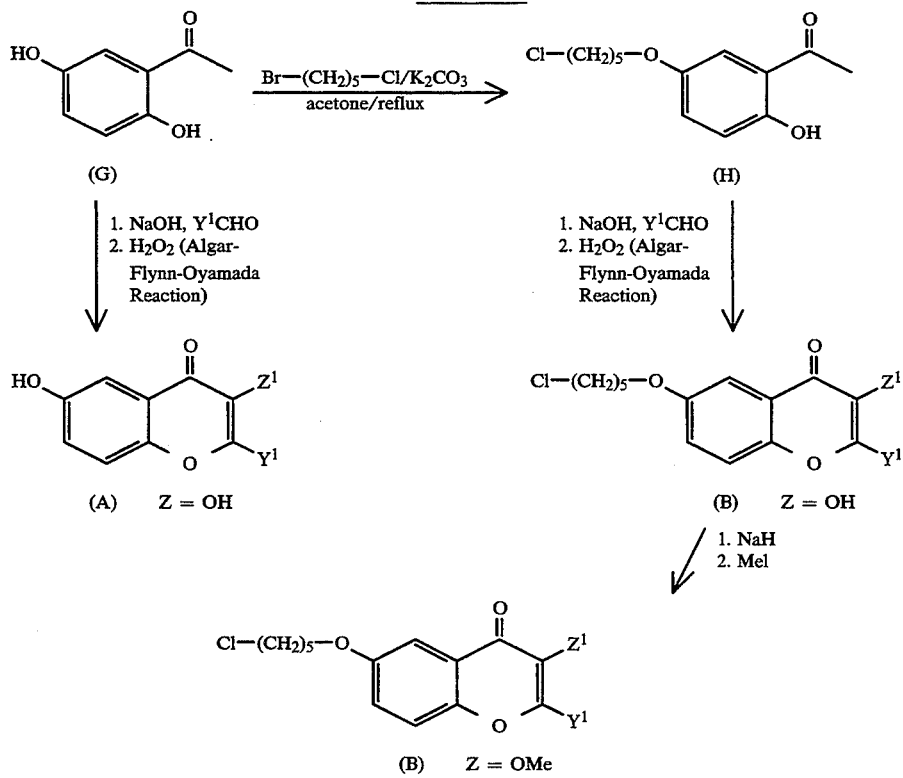

Schemes II and III illustrate the synthesis of Formula (A) or Formula (B) compounds when the desired Formula (A) compounds are not commercially available. Scheme II uses the Baker-Venkataraman (BV) rearrangement to make the desired Formula (A) or (B) compounds. The desired $Y^1$ group is introduced as an acid halide to give the diester of Formula (E) which is then treated with base under anhydrous conditions to induce the BV rearrangement. Subsequent acid treatment followed by treatment with aqueous base to hydrolyse the ester of the chromone hydroxyl group Formula (A) compounds. Alternatively, the desired B group from Formula I may be introduced before the BV rearrangement (shown here with B=(CH$_2$)$_5$ to give a Formula (F) compound) followed by treatment with the acid halide, the BV rearrangement, and acid treatment to give the desired Formula B compound.

In the cases for Formula I compounds where Z=OH or OR and Y =phenyl or substituted phenyl, then the chemistry of Scheme III is used to prepare Formula (A) or (B) compounds. Condensation of the acetophenone (G) with an aldehyde gives an intermediate chalcone which is then subjected to the Algar-Flynn-Oyamada (AFO) reaction (treatment with hydrogen peroxide under basic conditions) to give the desired Formula (A) compounds where $Z^1$=OH. Alternatively, the desired B group of Formula I may be introduced before the AFO reaction to give Formula (H) compounds. The Formula (H) compounds are reacted with an aldehyde and then subjected to the AFO reaction to give the desired Formula (B) compounds where $Z^1$=OH. If it is desired that $Z^1$=OR (where R is an alkyl group), then treatment of the Formula (B) compound (where $Z^1$=OH) with base and an alkylating agent (illustrated here with methyl iodide) will give the desired compounds.

Pharmaceutically acceptable acid addition salts of the compounds are formed with strong or moderately strong organic or inorganic acids by known methods. Exemplary of the salts which are included in this invention are maleate, fumarate, lactate, oxalate, methanesulfonate, ethansulfonate, benzenesulfonate, tartrate, citrate, hydrochloride, hydrobromide, sulfate, phosphate, quinate, and nitrate salts.

The Formula I and Formula II compounds are potent and selective for sigma binding sites and are effective in preclinical screens predictive of antipsychotic activity. The potency of these compounds in blocking radio ligand binding to sigma receptors was determined using the sigma receptor binding assay described in Example 77. In vivo antipsychotic potential was measured using two standard, accepted behavioral tests. The two tests used were: (1) Reversal of Amphetamine-Induced Hyperlocomotion (Example 78); and (2) Reversal of Phencyclidine-Induced Hyperlocomotion (Example 79). Potency in these tests was contrasted with potency to produce extrapyramidal side effects (Catalepsy test, Example 80). Selected compounds of Formula (I) were evaluated in these tests and compared to haloperidol, a widely-used antipsychotic agent; rimcazole, and BMY-14802, known sigma site binding agents; and clozapine, an atypical antipsychotic that appears relatively free of extrapyramidal side effects, but produces agranulocytosis upon chronic administration that limits its therapeutic potential.

The test data are shown in Table I below. As these data make clear, Formula I compounds are potent sigma binding site agents and are effective in at least one of the in vivo tests predictive of antipsychotic efficacy.

The compounds of Formula I and Formula III can be incorporated into convenient pharmaceutical dosage forms such as capsules, tablets, or injectable preparations. Solid or liquid pharmaceutical carriers can be employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling, and dissolving the ingredients, as appropriate, to give the desired oral or parenteral products.

Doses of the present compounds of Formula I and Formula III in a pharmaceutical dosage unit as described above will be an efficacious, nontoxic quantity selected from the range of 0.1–100 mg/kg of active compound, preferably 0.1–50 mg/kg. The selected dose is administered to a human patient expected to be benefited by a sigma binding site agent from 1–6 or more times daily, orally, rectally, by injection, or continuously by infusion. Oral dosage units for human administration preferably contain from 1 to 500 mg of active compound. Parenteral administration, generally uses lower doses.

The method of this invention of producing antagonism of sigma recepters in mammals, including humans, comprises administering internally to a subject expected to be benefited by a sigma receptor antagonist an effective amount therefore of a compound of Formula III.

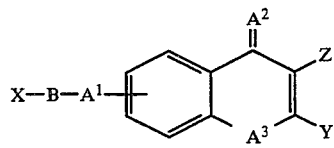

in which:
X is $-NR^1R^2$,

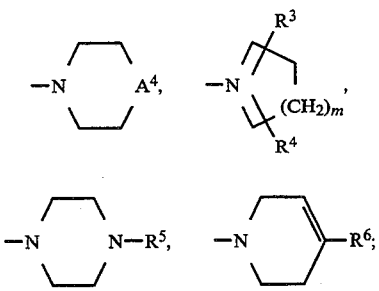

$R^1$ and $R^2$ are selected from the group consisting of —H, alkyl, a hydroxy-substituted $C_{1-6}$ alkyl, and benzyl, provided $R^1$ and $R^2$ are not H;

$R^3$ and $R^4$ are selected from the group consisting of —H, —OH, $C_{1-4}$ alkyl, hydroxy-substituted $C_{1-4}$ alkyl, benzyl, phenyl optionally substituted with —OH, —Cl, —F, —$OC_{1-4}$alkyl, —$C_{1-4}$ alkyl, —$CF_3$, and any accessible combination thereof;

$R^5$ is selected from the group consisting of —H, —$C_{1-6}$ alkyl, hydroxy-substituted $C_{1-6}$ alkyl, phenyl optionally substituted with —OH, —Cl, —F, —$OC_{1-4}$alkyl, —$CF_3$, and any accessible combination thereof;

$R^6$ is selected from the group consisting of phenyl optionally substituted with —OH, —Cl, —F, —$OC_{1-4}$ alkyl, —$C_{1-4}$ alkyl, —$CF_3$, and any accessible combination thereof;

m is 1, 2, or 3;

$A^1$, $A^2$, $A^3$, and $A^4$ independently are O or S;

Y is selected from the group consisting of cyclo$C_{3-7}$ alkyl, $C_{1-6}$ alkyl, thienyl, pyridyl, furanyl, quinolyl, phenyl optionally substituted with —OH, —Cl, —F, —$OC_{1-4}$ alkyl, $C_{1-4}$ alkyl, —$CF_3$, or any accessible combination thereof;

Z is —H, $C_{1-4}$ alkyl, or —$OR^7$;

$R^7$ is —H or $C_{1-4}$ alkyl; and

B is $C_{4-10}$ alkyl;

or pharmaceutically acceptable salts or hydrates thereof; provided that when B is $(CH_2)_4$, X is not $N(CH_3)_2$, $N(CH_2CH_3)_2$, piperidinyl, morpholinyl, pyrrolidinyl, or substituted piperazinyl.

Included in this invention are Formula (IV) compounds which are useful in preparing Formula (I) compounds:

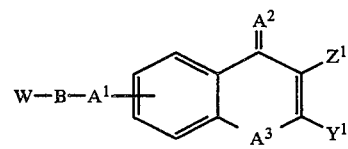

in which:
W is I, Br, or Cl;
$Z^1$ and $Y^1$ are Z and Y in Formula (I) or compounds readily convertible to Z and Y; and
$A^1$, $A^2$, and $A^3$ are as in Formula (I).

The following examples are illustrative of Formula (I) compounds and their preparation, and are given to illustrate the invention, but are not deemed to be limiting thereof. All percentages given throughout the specification are based on 100% by weight of the formulation.

EXAMPLE 1

6-[4-(Dimethylaminolbutoxy]-2-phenyl-4H-l,benzopyran-4-one hydrochloride

A mixture of 6-hydroxyflavone (5.0 g, 21 mmol), 1-bromo-4-chlorobutane (4.86 mL, 42 mmol), and potassium carbonate (12 g, 84 mmol) was refluxed in acetone for 24 hours. The solution was cooled to room temperature, filtered, and the solvent removed in vacuo. The residue was boiled with ether and filtered. Cooling gave 6.1 g (89%) of 6-(4-chlorobutoxy)-2-phenyl-4H-1-benzopyran-4-one as a white solid.

A mixture of 6-(4-chlorobutoxy)-2-phenyl-4H-1-benzopyran-4-one (3.0 g, 9 mmol) and sodium iodide (1.5 g, 10 mmol) in 125 mL of 2-butanone was refluxed for 96 hours. The solution was cooled to room temperature, filtered, and the solvent was removed in vacuo. The residue was stirred with 250 mL of dichloromethane and filtered. Removal of the solvent in vacuo gave the iodoflavone as a light yellow solid (3.8 g, 99%) that was used without further purification.

A mixture of 6-(4-iodobutoxy)-2-phenyl-4H-1-benzopyran-4-one (3.8 g, 9 mmol) and 40% aqueous dimethylamine (30 mL, 24 mmol) was refluxed in 100 mL of ethanol for 24 hours. The reaction mixture was cooled to room temperature (22° C.) and made basic with saturated aqueous sodium bicarbonate. The solution was concentrated in vacuo to approximately half its volume and extracted with ether. The combined ether layers were dried over sodium sulfate and the solvent removed in vacuo to give a yellow solid which was recrystallized to give 1.4 g of the free base as white crystals.

The free base (0.98 g, 28 mmol) was dissolved in 175 mL of ether and 29 mL of a 1.0 M solution of hydrogen chloride in ether was added. The resulting white precipitate was collected, washed with ether, and dried in vacuo to give 1.03 g of 6-[4-(dimethylamino)butoxy]-2-phenyl-4H-benzopyran-4-one hydrochloride: mp 215°–219° C.

EXAMPLE 2

6-[8-Dimethylamino)octoxy]3-2-phenyl-4H-1-benzopyran-4-one

A mixture of 5.0 g (21 mmol) of 6-hydroxyflavone, 22.8 g (84 mmol) of 1,8-dibromooctane, and 1 1.6 g (84 mmol) of potassium carbonate was refluxed in 250 mL of acetone for 48 hours. The reaction mixture was cooled to room temperature and filtered. The solutions were concentrated and cooled and 6.7 g of 6-(8-bromooctoxy)-2-phenyl-4H-benzopyran-4-one was collected in two crops. A mixture of 6-(8-bromooctoxy)-2-phenyl-4H-benzopyran-4-one (1.0 g, 2.3 mmol) and dimethylamine (40% wt./H$_2$O, 3.0 mL) was refluxed in ethanol (15 mL) for 2 hours. The reaction mixture was cooled to room temperature and then 5 mL of saturated sodium bicarbonate was added. The solvent was removed in vacuo and the residue triturated with 100 mL of ether. The mixture was filtered and the solutions were concentrated and cooled to give 0.6 g of 6-[8-(dimethylamino)octoxyl]-2-phenyl-4H-1-benzopyran-4-one: mp 73°–75° C.

EXAMPLE 3

6-[6-(4-(2-Hydroxyethyl)piperidinyl)hexoxy]-2-phenyl-4H-1-benzopyran-4-one hydrochloride A mixture of 6-(6-chlorohexoxy) flavone (Prepared from 6-hydroxyflavone and 1-bromo-6-chlorohexane by a manner similar to 6-(4-chlorobutoxy) flavone described in Example 1.) (2.00 g, 5.6 mmol), 4-(2-hydroxyethyl)piperidine (1.09 g, 8.4 mmol), sodium iodide (0.92 g, 6.1 mmol), and potassium carbonate (1.16 g, 8.4 mmol) in anhydrous DMF was stirred at 80°–90° C. for 24 hours. The reaction was cooled to room temperature and water (300 mL) was added to the flask. The resulting precipitate was collected by filtration and dissolved in methylene chloride (350 mL). This solution was washed with water (2×150 mL), brine (2×150 mL) and then the solution was dried over sodium sulfate. Removal of the solvent gave 2.32 g of the free base. The free base was dissolved in hot EtOAc and the solution filtered. Then 1 equivalent of a 1 M anhydrous solution of HCl in ether (Aldrich Chemical Co.) was added. The mixture was cooled in the freezer for 1 hour and the resulting solid was collected by vacuum filtration and recrystallized from methyl alcohol to give 6-[6-(4-(2-hydroxyethyl)piperidylhexoxy)]flavone hydrochloride which was dried over P2O5 in high vacuum at 100° C. (yield=2.29 g, 76%): mp 204°–206° C.

EXAMPLE 4

6-[6-Dimethylamino)hexoxy]-2-phenyl-4H-1-benzopyran-4-one hydrochloride

The compound was prepared by a method similar to Example 1 from 6-hydroxyflavone, 1-bromo-6-chlorohexane, and dimethylamine: mp 182°–185° C. (dec).

EXAMPLE 5

6-[6-(2-Hydroxyethylmethylamino)hexoxy]-2-phenyl-4H-1-benzopyran-4-one hydrochloride The compound was prepared by a method similar to Example 1 from 6-hydroxyflavone, 1-bromo-6-chlorohexane, and 2-hydroxyethylmethylamine: mp 134°–137° C.

EXAMPLE 6

6-[6(4-Hydroxypiperidinyl)hexoxy]-2-phenyl-4H-1-benzopyran-4-one hydrochloride

The compound was prepared by a method similar to Example 1 from 6-hydroxyflavone, 1-bromo-6-chlorohexane and 4-hydroxypiperidine: mp 219°–221° C.

EXAMPLE 7

6-[7-(Dimethylamino)heptoxy]-2-phenyl-4H-1-benzopyran-4-one

The compound was prepared by a method similar to Example 2 from 6-hydroxyflavone, 1,7-dibromoheptane and dimethylamine: mp 90°–91° C.

EXAMPLE 8

6-[9-(Dimethylamino)nonoxy]-2-phenyl-4H-1-benzopyran-4-one

The compound was prepared by a method similar to Example 2 from 6-hydroxyflavone, 1,9-dibromononane and dimethylamine: mp 52°–53° C.

EXAMPLE 9

6-[9-(4-Methylpiperazinyl)nonoxy]-2-phenyl-4H-1-benzopyran-4-one

The compound was prepared by a method similar to Example 2 from 6-hydroxyflavone, 1,9-dibromononane and 4-methyl piperazine: mp 77°–80° C.

EXAMPLE 10

6-[10-(Dimethylamino)decoxy]-2-phenyl-4H-1-benzopyran-4-one hydrochloride

The compound was prepared by a method similar to Example 2 from 6-hydroxyflavone, 1,10-dibromodecane and dimethylamine: mp 158°–160° C.

EXAMPLE 11

2-Cyclopentyl-6-[6-(4-Hydroxypiperidyl)hexoxy]-4H-1-benzopyran-4-one hydrochloride A mixture of 2',5'-dihydroxyacetophenone (150 g), 1-bromo-6-chlorohexane (186 g), and potassium carbonate (186 g) in 2500 mL of 2-butanone was refluxed for 16 hours. The solvent was removed in vacuo and the residue was stirred with 1000 mL of methylene chloride. After filtration, the filtrate was washed with 10% KOH (250 mL), water (250 mL), and brine (250 mL). The solution was dried over magnesium sulfate and the solvent was removed to give an oil which solidified overnight to give 210 g of 5'-(6-chlorohexoxy)-2'-hydroxyacetophenone as a yellow solid.

The acetophenone (63.7 g) was dissolved in 450 mL of pyridine. Then cyclopentane carbonyl chloride (45 g) was added. The solution was heated at 75° C. for 1.5 hours and then poured into 1200 mL of 3 N HCl. The solution was extracted with ethyl acetate (3×500 mL). The combined organic layers were extracted with 3 N HCl (2×500 mL), water (500 mL), 5% potassium carbonate (2×500 mL), and water (500 mL). After drying over magnesium sulfate the solvent was removed to give the ester as an oil (80.3 g) which was used directly in the next step.

Sodium hydride (7.9 g) was suspended in 400 mL of anhydrous DMF and the mixture was cooled to 0° C. where a solution of 80.3 g of the ester in 200 mL of anhydrous DMF was added dropwise. The mixture was stirred for 2 hours and then was quenched by the addition of 110 mL of acetic acid. This mixture was then poured into 1000 mL of a 1:1 solution of water and brine. This solution was extracted by ether (3×500 mL). The combined ether layers were washed with water (2×500 mL) and brine (2×500 mL) and then dried over magnesium sulfate. Removal of the solvent gave the diketone as a yellow solid (79.4 g).

The diketone was suspended in a solution of 4 mL of sulfuric acid in 400 mL of acetic acid. The mixture was refluxed for 3 hours. The solvent was removed in vacuo and the residue was dissolved in 800 mL of ethyl acetate. The solution was washed with water (400 mL), saturated sodium bicarbonate (2×500 mL) and brine (500 mL). After drying the solution over magnesium sulfate, the solvent was removed invacuo to give a solid which was recrystallized from ethyl acetate:hexane to give 31.2 g of 6-(6-chlorohexoxy)-2-cyclopentyl-4H-1-benzopyran-4-one.

The reaction between 6-(6-chlorohexoxy)-2-cyclopentyl-4H-1-benzopyran-4-one and 4-hydroxypiperidine was carried out in a manner similar to that of Example 3: mp 125°–126° C.

EXAMPLE 12

6-[5-(4-Hydroxypiperidinyl)pentoxy]-2-(4-methoxyphenyl-4H-1-benzopyran-4-one

The compound was prepared by a method similar to Example 11 from 2',5'-dihydroxyacetophenone, 4-methoxybenzoyl chloride, 1-bromo-5-chloropentane, and -hydroxypiperidine: mp 138°–139° C.

EXAMPLE 13

2-(3,4-Dimethoxyphenyl)6-[5-(4-hydroxypiperidinyl)pentoxy]-4H-1-benzopyran-4-one The compound was prepared by a method similar to Example 11 from 2',5'-dihydroxyacetophenone,3,4-dimethoxybenzoyl chloride, 1-bromo-5-chloropentane, and 4-hydroxypiperidine: mp 154°–155° C.

EXAMPLE 14

2-Cyclohexyl-6-[5-(4-hydroxypiperidinyl)pentoxy]-4H-1-benzopyran-4-one

The compound was prepared by a method similar to Example 11 from 2',5'-dihydroxyacetophenone, cyclohexanecarbonyl chloride, 1-bromo-5-chloropentane, and 4-hydroxypiperidine: mp 85°–86° C.

EXAMPLE 15

6-[5-(Dipropylamino)pentoxy]-2-(3-methoxyphenyl)-4H-1-benzopyran-4-one

The compound was prepared by a method similar to Example 11 from 2',5'-dihydroxyacetophenone, -methoxybenzoyl chloride, 1-bromo-5-chloropentane, and di-n-propyl amine: mp 80°–81° C.

EXAMPLE 16

6-[5-(Dipropylamino)pentoxy]-2-(4-methoxyphenyl)-4H-1-benzopyran-4-one

The compound was prepared by a method similar to Example 11 from 2',5'-acetophenone, 4-methoxybenzoyl chloride, 1-bromo-5-chloropentane, and di-n- propylamine: mp 63°–64° C.

EXAMPLE 17

2-(3,4-Dimethoxyphenyl)-6-[5-dipropylamino)pentoxyl]-4H-1-benzopyran-4-one hydrochloride The compound was prepared by a method similar to Example 11 from 2',5'-dihydroxyacetophenone, 3,4-dimethoxybenzoyl chloride, 1-bromo-5-chloropentane, and di-n-propylamine: mp 158°–159° C.

EXAMPLE 18

6-[5-(4-Hydroxypiperidinyl)pentoxy]-2-phenyl-4H-1-benzopyran-4-one

The compound was prepared by a method similar to Example 3 from 6-hydroxyflavone, 1-bromo-5-chloropentane and 4-hydroxypiperidine: mp 128°–129° C.

EXAMPLE 19

6-[7-(4-Hydroxypiperidinyl)heptoxy]-2-phenyl-4H-1-benzopyran-4-one

The compound was prepared by a method similar to Example 2 from 6-hydroxyflavone, 1-bromo-7- chloroheptane and 4- hydroxypiperidine: mp 135°–136° C.

EXAMPLE 20

7-[4-(Dimethylamino)butoxy]2-phenyl-4H-1-benzopyran-4-one

The compound was prepared by a method similar to Example 1 from 7-hydroxyflavone, 1-bromo-4-chlorobutane and dimethylamine: mp 95°–96° C.

EXAMPLE 21

5-[6-Dimethylamino)hexoxy]-2-phenyl-4H-1-benzopyran-4-one hydrochloride

To a solution of 5-hydroxyflavone (5.24 g) in 10 mL of dry DMF was added 1 equivalent of sodium hydride. The mixture was stirred until the evolution of hydrogen ceased. Then two equivalents of 1-bromo-6-chlorohexane were added and the solution was heated at 85° C. for approximately 72 hours. The mixture was then poured into 400 mL of water. A solid separated that was collected by filtration and recrystallized from ether to give 1.75 g of a mixture of 5-(6- chlorohexoxy) flavone and 5-(6-bromohexoxy)flavone. This mixture was then refluxed with 1.11 g of sodium iodide in 2-butanone for 48 hours. The mixture was cooled to room temperature and the solvent removed on a rotary evaporator. The residue was extracted with methylene chloride. Removal of the methylene chloride on a rotary evaporator gave 5-(6-iodohexoxy) flavone (1.5 g).

This compound then was dissolved in 50 mL of ethanol and refluxed with 5.5 mL of 40% aqueous dimethylamine overnight. Saturated sodium bicarbonate was added and then the solvent was removed on a rotary evaporator. The residue was extracted with ethyl acetate and the solvent removed to give the free base as a white solid. The solid was dissolved in ethanol and ethereal HCl was added. The product was collected by filtration and washed with ethanol and then with ether: mp 166°–168° C.

EXAMPLE 22

6-[4-(4-Hydroxypiperidinyl)butoxy]-2-phenyl-4H-1-benzopyran-4-one

The compound was prepared by a method similar to Example 3 from 6-hydroxyflavone, 1-bromo-4-chlorobutane and 4-hydroxyflavone: mp 124°–125° C.

EXAMPLE 23

6-[5-(4-Hydroxypiperidinyl)pentoxy]-2-isobutyl-4H-1-benzopyran-4-one

The compound was prepared by a method similar to Example 1i from 2′,5′-dihydroxyacetophenone, isobutyryl chloride, 1-bromo-5-chloropentane, and 4-hydroxypiperidine: mp 98°–99° C.

EXAMPLE 24

6-[8-(4-Hydroxypiperidinyl)octoxy]-2-phenyl-4H-1-benzopyran-4-one

The compound was prepared by a method similar to Example 2 from 6-hydroxyflavone, 1,8-dibromooctane and 4-hydroxypiperidine: mp 57°–58° C.

EXAMPLE 25

2-(3-Fluorophenyl)-6-[6-(4-hydroxypiperidinyl)hexoxy]-4H-1-benzopyran-4-one

The compound was prepared by a method similar to Example 11 from 2′,5′-dihydroxyacetophenone, 3-fluorobenzoyl chloride, 1-bromo-6-chlorohexane, and 4-hydroxypiperidine: mp 136°–137° C.

EXAMPLE 26

2-Cyclohexyl-6-[6-4-hydroxypiperidinyl)hexoxy]-4H-1-benzopyran-4-one hydrochloride The compound was prepared by a method similar to Example 11 from 2′,5′-dihydroxyacetophenone, cyclohexanecarbonyl chloride, 1-bromo-6-chlorohexane, and 4-hydroxypiperidine: mp 155°–156° C.

EXAMPLE 27

6-[6-(4-Hydroxypiperdinyl)hexoxy-2-(3-methoxyphenyl)-4H-1-benzopyran-4-one

The compound was prepared by a method similar to Example 11 from 2′,5′-dihydroxyacetophenone, 3-methoxybenzoyl chloride, 1-bromo-6-chlorohexane, and 4-hydroxypiperidine: mp 119°–120° C.

EXAMPLE 28

2-Phenyl-6-(6-piperidinylhexoxy)-4H-1-benzopyran-4-one hydrochloride

The compound was prepared by a method similar to Example 3 from 6-hydroxyflavone, 1-bromo-6-chlorohexane and piperidine: mp 176°–178° C.

EXAMPLE 29

6-(6-Morpholinylhexoxy)-2-phenyl-4H-1-benzopyran-4-one hydrochloride

The compound was prepared by a method similar to Example 3 from 6-hydroxyflavone, 1-bromo-6-chlorohexane and morpholine: mp 167°–170° C.

EXAMPLE 30

6-[5-(4-Hydroxypiperidyl)pentoxy]-2-3-methoxyphenyl)-4H-1-benzopyran-4-one

The compound was prepared by a method similar to Example 11 from 2′,5′-dihydroxyacetophenone, 3-methoxybenzoyl chloride-1-bromo-5-chloropentane, and 4-hydroxypiperidine: mp 115°–116° C.

EXAMPLE 31

2-(4-Chlorophenyl)-6-[6-(4-hydroxypiperidinyl)hexoxy]-4H-1-benzopyran-4-one

The compound was prepared by a method similar to Example 11 from 2′,5′-dihydroxyacetophenone, 4-chlorobenzoyl chloride, 1-bromo-6-chlorohexane, and 4-hydroxypiperidine: mp 127°–128° C.

EXAMPLE 32

2-(3-Chlorophenyl)-6-[6-(4-hydroxypiperidinyl)hexoxy]-4H-1-benzopyran-4-one

The compound was prepared by a method similar to Example 11 from 2′,5′-dihydroxyacetophenone, 3-chlorobenzoyl chloride, 1-bromo-6-chlorohexane, and 4-hydroxypiperidine: mp 120°–121° C.

EXAMPLE 33

6-[6-(4-Hydroxypiperidinyl)hexoxy]-2-(4-methoxyphenyl)-4H-1-benzopyran-4-one

The compound was prepared by a method similar to Example 11 from 2',5'-dihydroxyacetophenone, 4-methoxybenzoyl chloride, 1-bromo-6-chlorohexane, and 4-hydroxypiperidine: mp 134°–135° C.

EXAMPLE 34

2-Cyclohexyl-6-(piperidinylhexoxy)-4H-1-benzopyran-4-one hydrochloride

The compound was prepared by a method similar to Example 11 from 2',5,-dihydroxyacetophenone, cyclohexanecarbonyl chloride, 1-bromo-6-chlorohexane, and piperidine: mp 164°–165° C.

EXAMPLE 35

2-Cyclohexyl-6-(6-morpholinylhexoxy)-4H-1-benzopyran-4-one hydrochloride

The compound was prepared by a method similar to Example 11 from 2',5'-dihydroxyacetophenone, cyclohexanecarbonyl chloride, 1-bromo-6-chlorohexane, and morpholine: mp 167°–168° C.

EXAMPLE 36

7-[5-(4-Hydroxypiperidinyl)pentoxy]-2-phenyl-4H-1-benzopyran-4-one

The compound was prepared by a method similar to Example 3 from 7-hydroxyflavone, 1-bromo-5-chloropentane, and 4-hydroxypiperidine: mp 94°–95° C.

EXAMPLE 37

7-[6-(4-Hydroxypiperidinyl]hexoxy]-2-phenyl-4H-1-benzopyran-4-one

The compound was prepared by a method similar to Example 3 from 7-hydroxyflavone, 1-bromo-6-chlorohexane, and 4-hydroxypiperidine: mp 130°–131° C.

EXAMPLE 38

6-[-(4-Chlorophenyl)-1,2,3,6-tetrahydropyridyl)hexoxy]-2-phenyl-4H-1-benzopran-4-one hydrochloride The compound was prepared by a method similar to Example 3 from 6-hydroxyflavone, 1-bromo-6-chlorohexane, and 4-(4-chlorophenyl)-1,2,3,6-tetrahydropyridine: mp 213°–216° C.

EXAMPLE 39

6-[6-(4-Hydroxypiperidinyl)hexoxy]-3-methyl-2-phenyl-4H-1-benzopyran-4-one hydrochloride The compound was prepared by a method similar to Example 11 from 2',5'-dihydroxypropiophenone, benzoyl chloride, 1-bromo-6-chlorohexane, and 4-hydroxypiperidine: mp 175°–176° C.

EXAMPLE 40

2-Cyclohexyl-6-[6-(4-hydroxypiperidinyl)hexoxy]-3-methyl-4H-1-benzopyran-4-one hydrochloride The compound was prepared by a method similar to Example 11 from 2',5'-dihydroxypropiophenone, cyclohexanecarbonyl chloride, 1-bromo-6-chlorohexane, and 4-hydroxypiperidine: mp 109°–110° C.

EXAMPLE 41

6-[6-(4-Chlorophenyl)-4-hydroxypiperidinyl)hexoxy]-2-cyclopentyl-4H-1-benzopyran-4-one The compound was prepared by a method similar to Example 11 from 2',5'-dihydroxyacetophenone, cyclopentanecarbonyl chloride, 1-bromo-6-chlorohexane, and 4-(4-chlorophenyl)-4-hydroxypiperidine: mp 127°–128° C.

EXAMPLE 42

2-Cyclopentyl-6-[6-piperidinyl)hexoxy-4H-1-benzopyran-4-one hydrochloride

The compound was prepared by a method similar to Example 11 from 2',5'-dihydroxyacetophenone, cyclopentanecarbonyl chloride, 1-bromo-6-chlorohexane, and piperidine: mp 138°–139° C.

EXAMPLE 43

2-(4-Fluorophenyl)-6-[6-4-hydroxypiperidinyl)hexoxy]-4H-1-benzopyran-4-one

The compound was prepared by a method similar to Example 11 from 2',5'-dihydroxyacetophenone, 4-fluorobenzoyl chloride, 1-bromo-6-chlorohexane, and 4-hydroxypiperidine: mp 130°–131° C.

EXAMPLE 44

2-Cyclobutyl-6-[6-(4-hydroxypiperidinyl)hexoxy]-4H-1-benzopyran-4-one hydrochloride The compound was prepared by a method similar to Example 11 from 2',5'-dihydroxyacetophenone, cyclobutanecarbonyl chloride, 1-bromo-6-chlorohexane, and 4-hydroxypiperidine: mp 111°–113° C.

EXAMPLE 45

2-Cyclobutyl-6-(6-piperidinylhexoxy)-4H-1-benzopyran-4-one hydrochloride

The compound was prepared by a method similar to Example 11 from 2',5'-dihydroxyacetophenone, cyclobutanecarbonyl chloride, 1-bromo-6-chlorohexane, and piperidine: mp 165°–166° C.

EXAMPLE 46

6-[6-(4-Chlorophenyl)-4-hydroxypiperidinyl)-hexoxy]-2-cyclobutyl-4H-1-benzopyran-4-one The compound was prepared by a method similar to Example 11 from 2',5'-dihydroxyacetophenone, cyclobutanecarbonyl chloride, 1-bromo-6-chlorohexane, and 4-(4-chlorophenyl)-4- hydroxypiperidine: mp 127°–128° C.

EXAMPLE 47

2-(2-Chlorophenyl)-6-[6-(4-(4-chlorophenyl)-4-hydroxypiperidinyl)hexoxy]-4H-1-benzopyran-4-hydrochloride The compound was prepared by a method similar to Example 11 from 2',5'-dihydroxyacetophenone, 2-chlorobenzoyl chloride, 1-bromo-6-chlorohexane, and 4-4(4-chlorophenyl)-4-hydroxypiperidine: mp 180°–181° C.

EXAMPLE 48

2-(2-Chlorophenyl)-6-6-piperidinyl)hexoxy-4H-1-benzopyran-4-one hydrochloride

The compound was prepared by a method similar to Example 11 from 2',5'- dihydroxyacetophenone, -chlorobenzoyl chloride, 1-bromo-6-chlorohexane, and piperidine: mp 192°–193° C.

EXAMPLE 49

2-(2-Chlorophenyl)-6-(6-(4-hydroxypiperidinyl)hexoxy)-4H-1-benzopyran-4-one hydrochloride The compound was prepared by a method similar to Example 11 from 2',5'-dihydroxyacetophenone, 2-chlorobenzoyl chloride, 1-bromo-6-chlorohexane, and 4-hydroxypiperidine: mp 176°–177° C.

EXAMPLE 50

6-[6-(4-Hydroxypiperidinyl)hexoxy]-2-(2-thienyl)-4H-1-benzopyran-4-one hydrochloride The compound was prepared by a method similar to Example 11 from 2',5'-dihydroxyacetophenone, 2-thiophenecarbonyl chloride, 1-bromo-6-chlorohexane, and 4-hydroxypiperidine: mp 211°–212° C.

EXAMPLE 51

6-Piperidinyl-2-(2-thienyl)-4H-1-benzopyran-4-one hydrochloride

The compound was prepared by a method similar to Example 11 from 2',5'-dihydroxyacetophenone, -thiophenecarbonyl chloride, 1-bromo-6-chlorohexane, and piperidine: mp 184°–185° C.

EXAMPLE 52

6-[6-(4-(4-Chlorophenyl)-4-hydroxypiperidinyl)hexoxy]-2-(2-thienyl)-4H-1-benzopyran-4-one hydrochloride The compound was prepared by a method similar to Example 11 from 2',5'-dihydroxyacetophenone, 2-thiophenecarbonyl chloride, 1-bromo-6-chlorohexane, and 4-4(4-chlorophenyl)-4-hydroxypiperidine: mp 220°–221° C.

EXAMPLE 53

6-(6-(4-Methylpiperidinyl)hexoxy]-2-phenyl-4H-1-benzopyran-4-one hydrochloride

The compound was prepared by a method similar to Example 3 from 6-hydroxyflavone, 1-bromo-6-chlorohexane, and 4-methylpiperidine: mp 209°–214° C.

EXAMPLE 54

(±)-6-[6-(3-Hydroxypiperidinyl)hexoxy]-2-phenyl-4H-1-benzopyran-4-one hydrochloride The compound was prepared by a method similar to Example 3 from 6-hydroxyflavone, 1-bromo-6-chlorohexane, and 3-hydroxypiperidine: mp 197°–202° C.

EXAMPLE 55

6-[6-(4-Hydroxypiperidinyl)hexoxy]-2-phenyl-4H-1-benzopyran-4-one hydrochloride

A mixture of 5'-(6-chlorohexoxy)-2'-hydroxyacetophenone (32 g) and benzaldehyde (12 g) was dissolved in 250 mL of ethanol. A solution of 24 g of sodium hydroxide dissolved in 40 mL of water was added. This mixture was allowed to stand at room temperature for 6 hours. A solution of 8 g of sodium hydroxide dissolved in 40 mL of water was added, the solution was cooled to 15°–20° C., and then 20 mL of hydrogen peroxide (30% solution) was added and the solution was allowed to warm to room temperature and was stirred overnight. Then the solution's pH was adjusted to 3 using hydrochloric acid. The yellow precipitate was collected by vacuum filtration and washed with water, ethanol, and ether to give 16 g of 6-(6-chlorohexoxy)-3-hydroxy-4H-1-benzopyran-4-one.

Next, 10 g of 6-(6-chlorohexoxy)-3-hydroxy-4H-1-benzopyran-4-one was dissolved in 100 mL of tetrahydrofuran. Then 800 mg of sodium hydride was added followed by 8.3 mL of methyl iodide and the resulting solution was stirred at room temperature for 48 hours. The reaction was poured into water and extracted with ethyl acetate. The combined organic layers were washed with water and then with brine. After drying over sodium sulfate, the solvent was removed to give 8 g of 6-(6- chlorohexoxy)-3-methoxy-4H-1-benzopyran-4-one.

A mixture of 2 g of 6-(6-chlorohexoxy)-3-methoxy-4H-1-benzopyran-4-one, 1 g of sodium iodide, 0.6 g of potassium carbonate, and 1.4 g of 4-hydroxypiperidine was refluxed in butanone for 96 hours. The solvent was removed and the residue stirred with ethyl acetate and filtered. The solution was washed with water and then dried over sodium sulfate. The solvent was removed to give an oil which was chromatographed over silica gel to give 2 g of 6-[6-(4-hydroxypiperidinyl)hexoxy]-3-methoxy-4H-1-benzopyran-4-one which was converted to the hydrochloride salt by dissolving in ethyl acetate and adding 1 N ethereal HCL: mp 124°–125° C.

EXAMPLE 56

5-[4-(4-Hydroxypiperidyllbutoxy]-2-phenyl-4H-1-benzopyran-4-one hydrochloride

The compound was prepared by the method of Example 21 from 5-hydroxyflavone, 1-bromo-4-chlorobutane, and 4-hydroxypiperidine: mp 161°–163° C.

EXAMPLE 57

5-[5-(4-hydroxypiperidinyl)pentoxy]-2-phenyl-4H-1-benzopyran-4-one hydrochloride The compound was prepared by the method of Example 21 from 5-hydroxyflavone, 1-bromo-5-chloropentane, and 4-hydroxypiperidine: mp 184°–185° C.

EXAMPLE 58

5-[3-(4-hydroxypiperidinyl)propoxy]-2-phenyl-4H-1-benzopyran-4-one hydrochloride The compound was prepared by the method of Example 21 from 5-hydroxyflavone, 1-bromo-3-chloropropane, and 4-hydroxypiperidine: mp 213°–215° C.

EXAMPLE 59

6-[6-(N,N-Benzylmethylamino)hexoxy]-2-phenyl-4H-1-benzopyran-4-one hydrochloride The compound was prepared by the method of Example 3 from 6-hydroxyflavone, 1-bromo-6-chlorohexane, and N,N-benzylmethylamine: mp 178°–179° C.

EXAMPLE 60

6-(Pyrrolidylhexoxy)-2-phenyl-4H-1-benzopyran-4-one hydrochloride

The compound was prepared by the method of Example 3 from 6-hydroxyflavone, 1-bromo-6-chlorohexane, and pyrrolidine: mp 179°–181° C.

EXAMPLE 61

6-(6-Hexamethyleneiminohexoxy)-2-phenyl-4H-1-benzopyran-4-one hydrochloride

The compound was prepared by the method of Example 3 from 6-hydroxyflavone, 1-bromo-6-chlorohexane, and hexamethyleneimine: mp 173°–175° C.

EXAMPLE 62

5-[6-(4-hydroxypiperidinyl)hexoxy]-2-phenyl-4H-1-benzopyran-4-one hydrochloride

The compound was prepared by the method of Example 21 from 5-hydroxyflavone, 1-bromo-6-chlorohexane, and 4-hydroxypiperidine: mp 210°–211° C.

EXAMPLE 63

6-[6-(4-(2-Hydroxyethyl)piperazinyl)hexoxy]-2-phenyl-4H-1-benzopyran-4-one hydrochloride The compound was prepared by the method of Example 3 from 6-hydroxyflavone, 1-bromo-6-chlorohexane, and 4-(2-Hydroxyethyl)piperazine: mp 239°–241° C.

EXAMPLE 64

6-[5-(Dimethylamino)pentoxy]-2-phenyl-4H-1-benzopyran-4-one

The compound was prepared by the method of Example 3 from 6-hydroxyflavone, 1-bromo-5-chloropentane, and dimethylamine: mp 82°–83° C.

EXAMPLE 65

6-[6-(Diethylamino)hexoxy]-2-phenyl-4H-1-benzopyran-4-one hydrochloride

The compound was prepared by the method of Example 3 from 6-hydroxyflavone, reagent, and diethylamine: mp 159°–161° C.

EXAMPLE 66

6-[6-(4-(4-Chlorophenyl)piperazinyl)hexoxy]-2-phenyl-4H-1-benzopyran-4-one hydrochloride The compound was prepared by the method of Example 3 from 6-hydroxyflavone, 1-bromo-6-chlorohexane, and 4-(4-chlorophenyl)piperazine: mp 227°–229° C.

EXAMPLE 67

7-[8-(4-Hydroxypiperidinyl)octoxy]-2-phenyl-4H-1-benzopyran-4-one hydrochloride

The compound was prepared by the method of Example 2 from 7-hydroxyflavone, 1,8-dibromooctane, and 4-hydroxypiperidine

EXAMPLE 68

7-[4-(4-hydroxypiperidinyl)butoxy]-2-phenyl-4H-1-benzopyran-4-one hydrochloride

The compound was prepared by the method of Example 1 from 7-hydroxyflavone, 1-bromo-4-chlorobutane, and 4-hydroxypiperidine: mp 207°–209° C.

EXAMPLE 69

7-[7-(4-hydroxypiperidinyl)heptoxy]-2-phenyl-4H-1-benzopyran-4-one hydrochloride The compound was prepared by the method of Example 2 from 7-hydroxyflavone, 1,7-dibromoheptane, and 4-hydroxypiperidine: mp 143°–144° C.

EXAMPLE 70

6-(6-piperidinylhexoxy)-2-(3-pyridy)-4H-1-benzopyran-4-one hydrochloride

The compound was prepared by the method of Example 11 from 2',5'-dihydroxyacetophenone, 3-pyridylcarbonyl chloride, 1-bromo-6-chlorohexane, and piperidine: mp 192°–193° C.

EXAMPLE 71

6-(6-piperidinylhexoxy)-2-(4-pyridy)-4H-1-benzopyran-4-one hydrochloride

The compound was prepared by the method of Example 11 from 2',5'-dihydroxyacetophenone, 4-pyridylcarbonyl chloride, and piperidine: mp 186°–187° C.

EXAMPLE 72

6-[6-(4-Hydroxypiperidinyl)hexoxy]-2-(4-pyridyl)-4H-1-benzopyran-4-one hydrochloride The compound was prepared by the method of Example 11 from 2',5'-dihydroxyacetophenone, 4-pyridylcarbonyl chloride, and 4-hydroxypiperidine: mp 165°–166° C.

EXAMPLE 73

6-[6-(4-Hydroxypiperidinyl)hexoxy]-2-(3-pyridyl)-4H-1-benzopyran-4-one hydrochloride The compound was prepared by the method of Example 11 from 2',5'-dihydroxyacetophenone, 3-pyridylcarbonyl chloride, and 4-hydroxypiperidine:

EXAMPLE 74

An oral dosage form for administering the present compounds is produced by screening, mixing and filling into hard gelatin capsules the ingredients in the proportions shown in Table II.

EXAMPLE 75

The sucrose, calcium sulfate dihydrate, and Formula I compound shown in Table III are mixed and granulated in the proportions shown with a 10% gelatin solution. The wet granules are screened, dried, mixed with starch, talc and stearic acid, screened and compressed into a tablet.

EXAMPLE 76

6-[6-(4-Hydroxypiperidinyl)hexoxy]-3-methyl-2-phenyl-4H-1-benzopyran-4-one (75 mg) is dispersed in 25 ml of normal saline to prepare an injectable preparation.

EXAMPLE 77

Sigma and Dopamine Receptor Binding Assays

Two selective sigma receptor ligands, [$^3$H](+)-3-[3-hydroxyphenyl]-N-(1 propyl)piperidine [(+)-3-PPP] and [$^3$H] Ditolylguanidine (DTG), were used to label sigma sites in brain tissue.

The tissue preparation and assay conditions employed when using either of these ligands were essentially the same. Frozen whole guinea pig brains (obtained from Pel-Freez, Rogers, Ariz.) were homogenized in 10 volumes of ice-cold 0.32M sucrose. The resulting pellet was resuspended in 10 volumes of ice-cold 50 mM Tris-HCl (pH 7.4), incubated at 37° C. for 30 minutes, and centrifuged at 22,000×g for 20 minutes. The final tissue suspension was made in 50 mM Tris-HCl (pH 7.4) to a concentration of 20 mg original wet weight/mL. 800 μL of tissue suspension was added to tubes containing 5 nM [$^3$H] DTG or 4 nM [$^3$H] (+)-3-PPP, and either 10 μM haloperidol (to determine non-specific binding) or test compound. The final assay volume was 1 mL. The assay tubes were gently vortexed, and the binding reaction was carried out for 45 minutes at room temperature. The reaction was terminated by rapid filtration over Whatman GF/B glass fiber filters, which were then rinsed 3× with 5 mL of 50 mM Tris-HCl. Filter bound radioactivity was quantified using liquid scintillation spectrometry.

Dopamine receptor binding was determined using sulpiride. Rat striata were homogenized in 20 volumes of ice-cold 50 mM Tris-HCl (pH 7.5), and the resulting homogenate was centrifuged at 48,000×g for 10 minutes. The resulting pellet was resuspended in the original volume of 50 mM Tris HCl and centrifuged as previously described. The final pellet was resuspended in 50 mM Tris-HCl (pH 7.5) containing 100 mM NaCl to a tissue concentration of 3.75 mg original wet weight/mL. 800 μL of tissue suspension was added to tubes containing 3 nM [$^3$H] sulpiride and either 10 μM unlabeled haloperidol (to determine non-specific binding) or test compound. The binding reaction was terminated after 60 minutes at room temperature by rapid filtration over presoaked (0.3% PEI) Whatman GF/B glass fiber filters. The filters were then washed 3× with 5 mL of 50 mM Tris-HCl containing 100 mM NaCl, and filter bound radioactivity was quantified using liquid scintillation spectrometry.

The results of these receptor binding assays are given in Table I.

EXAMPLE 78

Reversal of Amphetamine-Induced Hyperlocomotion

Opto-varimex locomotor monitors (Columbus Instruments, Columbus, Ohio) were used to assess locomotor activity. The monitors consist of a 37×37 cm square plexiglass open field surrounded by an outer enclosure housing a 15×15 array of infrared photobeams. Placement of the mouse in the open field interrupts one or more beams. Movement is detected by successive interruption of more than one beam (setting: box size—1). The monitors were placed on separate shelves in a dark test room. An IBM compatible computer (Compaq) monitored beam interruptions and calculated indices of locomotor activity (distance travelled, time ambulating) and stereotype behavior (number of small movements, time in stereotypy or small movements). Because the dose of amphetamine in these studies was too low to produce selective increases in stereotyped behavior, distance travelled was the primary dependent variable.

Male CF1 mice (25–30 g) were obtained from Harlan Sprague Dawley (Indianapolis, (N) and group-housed with free access to food and water for at least four days prior to testing. All tests took place during the light period of a 12:12 hour light-dark cycle. Each daily test consisted of one group of mice receiving a vehicle injection and an injection of amphetamine as the agonist. One group received two vehicle injections, and one or more groups received test compound plus amphetamine. Test compounds or the appropriate vehicles were administered 20 minutes prior to the locomotor test in studies using an intraperitoneal (i.p.) route of administration with mice, 30 minutes prior to test session for studies using an j.p. route of administration to rats, 45 minutes prior to the test session for studies using an oral (p.o.) route of administration with mice and 55 minutes prior to the locomotor test for studies using a p.o. route of administration to rats. Amphetamine (1.5 mg/kg, i.p.) or saline vehicle was injected 10 minutes prior to the test session for all studies.

For initial screening, compounds were administered i.p. to mice at one or more doses, chosen either on the basis of potency of similar compounds, or chosen by reference to toxic doses (e.g., 1/5 the catalepsy TD$_{50}$). A dose of test drug was considered effective if the mean distance travelled by the drug-plus-amphetamine treated mice fell more than 2.33 standard errors (99% confidence limits of the drug-plus amphetamine group) below the mean for the vehicle-plus-amphetamine group. Compounds that appeared active in the initial screen were re-evaluated at a minimum of three doses, including the dose that appeared effective in the initial screen. For this and all remaining studies (i.e., oral activity, effects in rats) the minimally effective dose (MED) was then estimated as the lowest dose for which a separate variance I test indicated that distance travelled by the drug-plus-amphetamine treated group differed significantly from distance travelled by the vehicle-plus- amphetamine group (<0.05).

The test results for selected compounds are shown in Table I.

EXAMPLE 79

Reversal of Phencyclidine-Induced Hyperlocomotion

The procedure and data analysis were identical to that reported above for reversal of amphetamine hyperlocomotion with the exception that 3 mg/kg phencyclidine was injected in place of amphetamine 10 minutes prior to the test session. The test results are shown in Table I.

EXAMPLE 80

Induction of Haloperidol-like Catalypsy

Male CF1 mice (25–30 g) (Harlan Sprague-Dawley) were injected with test compound or the appropriate vehicle 30 minutes prior to the test. At the time of the test the front paws of the mouse were placed on a 6 mm diameter rod which was mounted between the side walls of the apparatus, 39 mm above the floor. Gentle pressure was applied from the forefinger to immobilize the animal, with its back in a slightly arched (concave) position. The experimenter then released the mouse and recorded the latency to recover normal posture, as defined by return of at least one forepaw to the floor or placement of one hindlimb on the bar. A mouse was considered cataleptic if it did not recover normal posture within 30 seconds. Each mouse was given up to three opportunities to demonstrate catalepsy. A minimum of 6 mice were tested at each drug dose and a $TD_{50}$ for producing catalepsy was calculated according to the method of Litchfield and Wilcoxin (1949). $TD_{50}$ values for lead compounds and reference compounds were confirmed in side-by-side studies by an experimenter blind to treatment conditions. The test results are shown in Table I.

TABLE I
SUMMARY OF IN VITRO AND IN VIVO TESTING

| Drug (Name or Example No.) | Receptor Potency | | | | | |
|---|---|---|---|---|---|---|
| | Sigma ($IC_{50}$, nMol) | | $D_2$ ($K_i$, nMol) | Induced Locomotion | | Catalepsy |
| | DTG | PPP | | Amphetamine | PCP | |
| Clozapine | 15,000 | 34,600 | 350 | 1 | | NE (4) |
| Haloperidol | 7 | 4 | 0.67 | 0.075 | 0.15 | 0.14 |
| Rimcazole | 1,620 | 1,400 | 22,520 | 20 | >20 | NE |
| BMY14802 | 237 | 319 | 3,000 | 15 | | NE |
| 4 | 432 | 335 | 5,550 | 30 | NE (30) | 38 |
| 6 | 100 | 124 | 3,630 | 5.0 | 15 | 61 |
| 26 | 88 | 46 | 25,000 | 20 | | 50 |
| 39 | 36 | 43 | 2,700 | 25 | | NE (250) |
| 28 | 100 | 54 | 4,445 | 20 | 30 | <30 |
| 34 | 54 | 32 | 7,650 | 10 | | 30 |
| 37 | 45 | 70 | 6,000 | 30 | | |
| 49 | 47 | 29 | 4,050 | 30 | | |
| 29 | 713 | 237 | 18,700 | 10 | | 38 |

NE = no effect to dose shown

TABLE II

| Ingredients | Amounts |
|---|---|
| 6-[6-(4-Hydroxypiperidinyl)hexoxy]-3-methyl-2-phenyl-4H-1-benzopyran-4-one | 50 mg |
| magnesium stearate | 5 mg |
| lactose | 75 mg |

TABLE III

| Ingredients | Amounts |
|---|---|
| 6-[6-(4-Hydroxypiperidinyl)-hexoxy]-3-methyl-2-phenyl-4H-1-benzopyran-4-one | 100 mg |
| calcium sulfate dihydrate | 20 mg |
| sucrose | 150 mg |
| starch | 20 mg |
| talc | 5 mg |
| stearic acid | 3 mg |

The invention being thus described, it will be obvious that the same may be varied in many ways. Such variations are not to be regarded as a departure from the spirit and scope of the invention and all such modifications are intended to be included within the scope of the claims.

What is claimed is:

1. A compound represented by the formula:

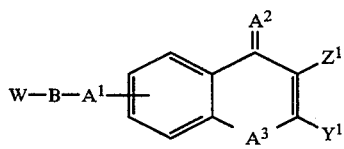

in which:
W is I, Br, or Cl;
$Z^1$ is —H, $C_{1-4}$ alkyl, or —OR;
R is —H or $C_{1-4}$ alkyl;
$Y^1$ is selected from the group consisting of cyclo$C_{3-7}$ alkyl, unsubstituted phenyl and phenyl substituted with —OH, —Cl, —F, —$OC_{1-4}$ alkyl, $C_{1-4}$ alkyl, —$CF_3$ or any accessible combination thereof;
$A^1$, $A^2$, and $A^3$ independently are O or S; and
B is $C_{4-10}$ alkyl.

2. A compound of claim 1 represented by the formula:

II

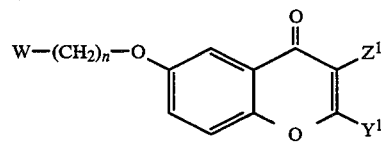

in which n is 4 to 10, and W, $Y^1$, and $Z^1$ are as in claim 1.

3. A compound of claim 2 in which $Z^1$ is methyl and $Y^1$ is phenyl.
4. A compound of claim 3 in which n is 6.
5. A compound of claim 2 in which $Z^1$ is hydrogen and $Y^1$ is phenyl.
6. A compound of claim 2 in which $Y^1$ is fluorophenyl and n is 6.
7. A compound of claim 2 in which $Y^1$ is cyclohexyl, $Z^1$ is methyl or hydrogen, and n is 5 or 6.
8. A compound of claim 2 in which $Y^1$ is methoxyphenyl and n is 4 or 5.
9. A compound of claim 2 in which $Y^1$ is chlorophenyl and n is 6.
10. A compound of claim 2 in which $Y^1$ is cyclopentyl and n is 6.
11. A compound of claim 2 in which $Y^1$ is cyclobutyl and n is 6.
12. A compound of claim 2 in which $Y^1$ is 3,4-dimethoxyphenyl and n is 5.
13. A compound of claim 2 in which $Y^1$ is phenyl and $Z^1$ is $C_{1-4}$ alkyl.
14. A compound of claim 2 in which $Y^1$ is phenyl and $Z^1$ is —OR.
15. A compound of claim 2 in which n is 5 to 10.
16. A compound of claim 2 in which n is 5 to 8.
17. A compound of claim 2 in which n is 6.

* * * * *